United States Patent [19]

Horie et al.

[11] 4,436,835

[45] Mar. 13, 1984

[54] PROCESS FOR PREPARATION OF CATALYSTS

[75] Inventors: Shigeru Horie, Gouzu; Yasuo Yamamoto, Niigata; Takeo Ikarashi, Niitsu, all of Japan

[73] Assignee: Mitsubishi Gas Chemical Company Inc., Tokyo, Japan

[21] Appl. No.: 477,755

[22] Filed: Mar. 22, 1983

[30] Foreign Application Priority Data

Mar. 24, 1982 [JP] Japan ................................. 57-46497

[51] Int. Cl.³ ........................................... B01J 27/14
[52] U.S. Cl. .................................... 502/208; 502/150; 560/239
[58] Field of Search ................... 252/429 R, 430, 437; 560/239

[56] References Cited

U.S. PATENT DOCUMENTS

| | | | |
|---|---|---|---|
| 2,189,655 | 2/1940 | Ruthruff | 252/437 X |
| 2,230,980 | 2/1941 | Ruthruff | 252/437 X |
| 2,770,656 | 11/1956 | Pye | 252/437 X |
| 4,179,358 | 12/1979 | Swift et al. | 252/537 X |
| 4,382,877 | 5/1983 | Kehl | 252/437 |

FOREIGN PATENT DOCUMENTS

| | | | |
|---|---|---|---|
| 53-71008 | 6/1978 | Japan | 252/473 |
| 54-12315 | 1/1979 | Japan | 252/476 |

*Primary Examiner*—William G. Wright
*Attorney, Agent, or Firm*—Sherman & Shalloway

[57] ABSTRACT

Disclosed is a process for the preparation of a catalyst for the synthesis of methyl formate by dehydrogenating methanol in the gaseous phase, said process being characterized in that (A) at least one phosphate selected from the group consisting of copper phosphates, zinc phosphates and aluminum phosphates, and (B) at least one chloride selected from the group consisting of copper chlorides, zinc chloride, aluminum chloride, alkali metal chlorides and alkaline earth metal chlorides and/or (C) at least one compound selected from the group consisting of alkali metal compounds (exclusive of halides) and alkaline earth metal compounds (exclusive of halides) are added to copper oxide, zinc oxide and aluminum oxide.

The catalyst obtained according to this process has a high activity for preparing methyl formate by dehydrogenating methanol in the gaseous phase, and this catalyst is excellent in the heat resistance and durability and has a high mechanical strength.

7 Claims, No Drawings

PROCESS FOR PREPARATION OF CATALYSTS

BACKGROUND OF THE INVENTION (1) Field of the Invention

The present invention relates to a process for the preparation of catalysts. More particularly, the present invention relates to a process for the preparation of catalysts for use in synthesizing methyl formate by dehydrogenating methanol in the gaseous phase.

(2) Description of the Prior Art

Many catalysts are known to be effective for synthesizing methyl formate by dehydrogenating methanol in the gaseous phase. As catalysts having an especially high activity, there can be mentioned catalysts consisting of copper, zirconium and zinc or copper, zirconium, zinc and aluminum (see Japanese Patent Application Laid-Open Specification No. 71008/78) and catalysts consisting of copper oxide, zinc oxide and aluminum oxide (see Japanese Patent Application Laid-Open Specification No. 12315/79).

In these known catalysts, the main component is ordinarily copper, and these catalysts are prepared through a calcination treatment conducted at a high temperature exceeding 400° C. Accordingly, in the case where such catalyst is used after it has been granulated into tablets by the tableting method and packed in a reaction vessel, it is seen that the mechanical strength of the catalyst is drastically reduced in a short time from the initiation of the reaction. The catalyst having a reduced mechanical strength is readily powdered while it is used, and therefore, the pressure difference between the inlet and the outlet of the reaction vessel is increased and there is a risk that the operation is hindered. Accordingly, the above-mentioned known catalysts are still insufficient in the adaptability to the practical operation.

SUMMARY OF THE INVENTION

We made researches with a view to obviating the above-mentioned practical defect of the conventional copper-zinc-aluminum catalysts for the synthesis of methyl formate having a relatively high activity, and as the result, it was found that if specific components are incorporated in a copper oxide-zinc oxide-aluminum oxide catalyst, the activity, heat resistance and durability can be increased over those of the conventional catalysts and the mechanical strength can highly be improved. We have now completed the present invention based on this finding.

It is therefore a primary object of the present invention to provide a catalyst for the synthesis of methyl formate by dehydrogenating methanol in the gaseous phase, which has a high activity, high heat resistance and durability and a high mechanical strength.

More specifically, in accordance with the present invention, there is provided a process for the preparation of a catalyst for the synthesis of methyl formate by dehydrogenating methanol in the gaseous phase, said process being characterized in that (A) at least one phosphate selected from the group consisting of copper phosphates, zinc phosphates and aluminum phosphates, and (B) at least one chloride selected from the group consisting of copper chlorides, zinc chloride, aluminum chloride, alkali metal chlorides and alkaline earth metal chlorides and/or (C) at least one compound selected from the group consisting of alkali metal compounds (exclusive of halides) and alkaline earth metal compounds (exclusive of halides) are added to copper oxide, zinc oxide and aluminum oxide.

DETAILED DESCRIPTION OF THE INVENTION

In connection with a mixture of copper oxide, zinc oxide and aluminum oxide, which is used in the present invention, the preparation process or quality is not particularly critical. This mixture can be prepared according to various methods. From the practical viewpoint, there are ordinarily adopted a method in which preformed powders of copper oxide, zinc oxide and aluminum oxide are homogeneously mixed, a method in which an alkali metal carbonate or the like is added to a mixed aqueous solution of water-soluble salts of copper, zinc and aluminum to cause coprecipitation and the formed coprecipitate is calcined to form a mixture of oxides, a method in which compounds capable of being converted to copper oxide and zinc oxide, respectively, by calcination are mixed with aluminum oxide or alumina sol and the mixture is calcined, and a method in which water-soluble salts of copper, zinc and aluminum are mixed together and an alkali metal hydroxide is added to a solution of this mixture to form a coprecipitate of oxides. There is especially preferably adopted a method in which water-soluble salts of copper and zinc are sufficiently mixed, an alkali metal hydroxide is added to a solution of this mixture to coprecipitate copper oxide and zinc oxide and alumina sol is added to the coprecipitate.

As typical instances of the component (A), there can be mentioned cupric phosphate, zinc phosphate, aluminum phosphate, aluminum monohydrogenphosphate and aluminum dihydrogenphosphate.

As the component (B), there can be mentioned, for example, cuprous chloride, cupric chloride, zinc chloride, aluminum chloride, sodium chloride, lithium chloride, cesium chloride, potassium chloride, calcium chloride, strontium chloride and barium chloride.

Any of compounds other than halides can be used as the component (C) without any particular restriction. From the practical viewpoint, there are ordinarily used oxides, hydroxides, inorganic acid salts such as carbonates, phosphates, nitrates and sulfates, and organic acid salts such as formates, acetates and oxalates. As typical instances, there can be mentioned lithium oxide, cesium oxide, magnesium oxide, calcium oxide, strontium oxide, sodium hydroxide, potassium hydroxide, lithium hydroxide, cesium hydroxide, magnesium hydroxide, calcium hydroxide, barium hydroxide, strontium hydroxide, sodium carbonate, potassium carbonate, lithium carbonate, cesium carbonate, strontium carbonate, calcium carbonate, barium carbonate, sodium hydrogencarbonate, potassium hydrogencarbonate, lithium hydrogencarbonate, sodium monohydrogenphosphate, sodium dihydrogenphosphate, sodium phosphate, potassium monohydrogenphosphate, potassium dihydrogenphosphate, potassium phosphate, lithium phosphate, magnesium phosphate, magnesium hydrogenphosphate, calcium monohydrogenphosphate, calcium dihydrogenphosphate, calcium phosphate, strontium monohydrogenphosphate, strontium phosphate, barium monohydrogenphosphate, sodium nitrate, potassium nitrate, lithium nitrate, magnesium nitrate, calcium nitrate, barium nitrate, strontium nitrate, cesium nitrate, sodium sulfate, potassium sulfate, lithium sulfate, magnesium sulfate, calcium sulfate, barium sulfate, strontium sulfate, cesium sulfate, sodium hydrogensulfate, potassium hydrogensulfate, lithium hydrogensulfate, sodium formate, potassium formate, lithium formate, cesium formate, magnesium formate, calcium formate, barium formate, strontium formate, sodium acetate, potassium acetate, lithium acetate, magnesium acetate, calcium acetate, barium acetate, cesium acetate, sodium oxalate, potassium oxalate, lithium oxalate, magnesium oxalate, calcium oxalate, sodium hydrogenoxalate, potassium hydrogenoxalate and lithium hydrogenoxalate.

Furthermore, compounds containing two or more of the foregoing compounds in one molecule, for example, double salts such as $2Na_3PO_4 \cdot Ca(PO_4)_2$, may be used.

In the present invention, as the combination of the components (A), (B) and (C) to be added to copper oxide, zinc oxide and aluminum oxide, there can be mentioned three combinations; that is, (1) the three-component combination comprising the components (A), (B) and (C), the two-component combination comprising the components (A) and (B) and the two-component combination comprising the components (A) and (C). In the case where the component (A) is formed from the components (B) and (C) when the components (B) and (C) are used in combination, for example, in the case where cupric chloride and sodium phosphate are used as the components (B) and (C), respectively, and cupric phosphate as the component (A) is formed, even if the component (A) is not particularly added, it can be considered that this combination corresponds to any one of the foregoing three combinations.

The amounts used of the respective compounds will now be described. Zinc oxide is used in an amount of 0.01 to 10 moles, preferably 0.1 to 5 moles per 10 moles of copper oxide and aluminum oxide is used in an amount of 0.01 to 10 moles, preferably 0.1 to 5 moles, per 10 moles of copper oxide. The component (A) is used in an amount of 0.01 to 10 moles, preferably 0.05 to 5 moles, per 10 moles of copper oxide. When the components (B) and (C) are respectively added, the component (B) is used in an amount of 0.01 to 10 moles, preferably 0.05 to 5 moles, per 10 moles of copper oxide, and the component (C) is used in an amount of 0.01 to 10 moles, preferably 0.05 to 5 moles, per 10 moles of copper oxide.

According to customary procedures, the so-obtained mixture is dried and is then molded after or without calcination, and the molded mixture is reduced to obtain a catalyst activity for the synthesis of methyl formate.

Drying is carried out at a temperature of from normal temperature to 200° C., preferably 80° to 150° C., under atmospheric pressure or reduced pressure. Calcination is carried out at a temperature of 200° to 1000° C., preferably 300° to 800° C., in the atmosphere of air or an inert gas such as nitrogen gas, or a mixture of an inert gas and air. Molding is carried out by using a perforated plate or a tableting machine with or without addition of a lubricant such as graphite. Reduction is carried out in a reducing gas such as hydrogen, carbon monoxide or a mixed gas thereof at an elevated temperature of 150° to 400° C. Furthermore, reduction can be accomplished by using hydrogen and carbon monoxide formed by decomposition of methanol when methanol is contacted with the heated catalyst.

Reaction conditions adopted for preparing methyl formate by dehydrogenating methanol in the gaseous phase by using the catalyst obtained according to the present invention will now be described. The reaction temperature is 100° to 400° C., preferably 150° to 350° C. The space velocity is 100 to 50000 $hr^{-1}$, preferably 500 to 30000 $hr^{-1}$. The reaction pressure is not more than 50 $Kg/cm^2$ G, and it is preferred that the reaction be carried out under a pressure of up to 10 $Kg/cm^2$ G or a reduced pressure. If necessary, the reaction can be carried out in the presence of a gas such as hydrogen, carbon monoxide or nitrogen in an amount of about 0.1 to about 2 moles per mole of methanol.

The catalyst obtained according to the present invention exerts a high activity when it is used for preparing methyl formate by dehydrogenating methanol in the gaseous phase, and this catalyst is excellent in heat resistance and durability and has a high mechanical strength. Accordingly, this catalyst can be used industrially advantageously.

The present invention will now be described in detail with reference to the following Examples that by no means limit the scope of the invention.

EXAMPLES 1 THROUGH 10

An aqueous solution containing copper nitrate and zinc nitrate at a predetermined ratio was mixed with an aqueous solution of sodium hydroxide to obtain a coprecipitate of copper oxide and zinc oxide. The coprecipitate was recovered by filtration and then washed, and alumina sol was added to the coprecipitate so that a predetermined composition was obtained. Predetermined amounts of the component (A) and the component (B) and/or the component (C) were added to the so-obtained copper oxide/zinc oxide/aluminum oxide mixture. The so-obtained mixture having a predetermined composition was dried at 115° C. and calcined at 600° C. in air current. Then, 3% by weight of graphite was added to the calcined mixture, and the mixture was granulated according to the tableting method. A reaction vessel having an inner diameter of 10 mm was packed with 10 cc of the tableted catalyst and the catalyst was heated at 200° C. in a hydrogen current for 6 hours to effect reduction. Methanol vapor was introduced into the reaction vessel at a constant speed corresponding to the space velocity of 3500 $hr^{-1}$, and the experiment was continuously carried out for 20 days under atmospheric pressure at a constant reaction temperature. The composition of the respective components, the temperature for the methyl formate-forming reaction and the obtained results are shown in Table 1.

The mechanical strength of the tableted catalyst was determined before the reduction and after the reaction (after the continuous experiment, the catalyst was taken out from the reaction vessel, the surface of the catalyst was partially oxidized in air at room temperature and the measurement was made on the resulting stabilized catalyst) according to the following method.

A cylindrical drum having an inner diameter of 100 mm and having a net of 14 mesh according to JIS spread on the circumferential face thereof was charged with 10 g of the tableted catalyst before the reduction or after the reaction, and the drum was rolled at 160 rpm for 20 minutes. The amount of the catalyst left in the drum was measured and the powdering ratio was calculated according to the following formula:

$$\text{Powdering Ratio (\%)} = \frac{(\text{amount (g) of charged sample}) - (\text{amount (g) of sample left in drum})}{(\text{amount (g) of charged sample})} \times 100$$

The crushing strength of the tableted catalyst before the reduction with respect to the longitudinal direction (the direction of the central axis) was measured by a small tester (Model PSP-300 supplied by Fujii Seiki Co.).

The powdering ratio and crushing strength determined according to the above procedures are shown in Table 1.

EXAMPLE 14

A copper oxide/zinc oxide/aluminum oxide mixture was prepared in the same manner as in Examples 1 through 10. Separately, aqueous solutions containing equivalent amounts of cupric chloride and tertiary so-

TABLE 1

| Example No. | CuO | ZnO | $Al_2O_3$ | Component (A) | Component (B) | Component (C) | Reaction Temperature (°C.) |
|---|---|---|---|---|---|---|---|
| 1 | 10 | 0.5 | 1 | $Cu_3(PO_4)_2$ 0.33 | NaCl 0.2 | $Na_3PO_4$ 0.17 | 280 |
| 2 | 10 | 0.5 | 1 | $Cu_3(PO_4)_2$ 0.33 | — | $Na_3PO_4$ 0.17 | 270 |
| 3 | 10 | 0.5 | 3 | $Cu_3(PO_4)_2$ 0.33 | — | HCOONa 2 | 280 |
| 4 | 10 | 0.5 | 1 | $Cu_3(PO_4)_2$ 0.33 $Zn_3(PO_4)_2$ 0.33 | NaCl 2 | — | 300 |
| 5 | 10 | 3 | 0.5 | $Cu_3(PO_4)_2$ 0.33 | $BaCl_2$ 0.1 | NaOH 0.5 | 330 |
| 6 | 10 | 0.5 | 1 | $Cu_3(PO_4)_2$ 0.05 | $CaCl_2$ 0.1 | $Ca_3(PO_4)_2$ 2 | 290 |
| 7 | 10 | 0.5 | 1 | $Cu_3(PO_4)_2$ 0.33 | $CaCl_2$ 0.1 | $CaSO_4$ 0.5 | 280 |
| 8 | 10 | 0.1 | 1 | $Cu_3(PO_4)_2$ 0.33 | $ZnCl_2$ 0.5 | $Li_3PO_4$ 0.5 | 280 |
| 9 | 10 | 0.5 | 1 | $Cu_3(PO_4)_2$ 2 | KCl 0.5 | $K_3PO_4$ 1 | 260 |
| 10 | 10 | 0.5 | 1 | $Cu_3(PO_4)_2$ 0.33 | $AlCl_3$ 0.05 | $K_2CO_3$ 0.3 | 280 |

| Example No. | Number of Elasped Days | Conversion (mole %) of Methanol | Yield (mole %) of Methyl Formate | Selectivity (mole %) of Methyl Formate | Before Reduction Powdering Ratio (% by weight) | Before Reduction Crushing Strength (Kg/cm²) | Powdering Ratio (% by weight) after Reaction * |
|---|---|---|---|---|---|---|---|
| 1 | 1 | 53.9 | 49.5 | 91.9 | 3.7 | 250 | 9.9 |
|   | 10 | 53.9 | 49.9 | 92.6 | | | |
|   | 20 | 52.5 | 48.9 | 93.1 | | | |
| 2 | 1 | 50.5 | 44.9 | 88.9 | 3.3 | 225 | 5.5 |
|   | 10 | 47.5 | 44.2 | 93.1 | | | |
|   | 20 | 46.7 | 43.7 | 93.5 | | | |
| 3 | 1 | 51.5 | 44.9 | 87.2 | 1.1 | 276 | 3.7 |
|   | 10 | 50.5 | 44.6 | 88.3 | | | |
|   | 20 | 49.8 | 44.1 | 88.6 | | | |
| 4 | 2 | 52.8 | 47.2 | 89.3 | 5.4 | 233 | 12.7 |
|   | 10 | 50.2 | 45.2 | 90.1 | | | |
|   | 20 | 49.1 | 44.4 | 90.5 | | | |
| 5 | 1 | 55.3 | 48.0 | 86.8 | 3.8 | 235 | 7.2 |
|   | 10 | 53.7 | 47.5 | 88.5 | | | |
|   | 20 | 52.3 | 46.5 | 88.9 | | | |
| 6 | 1 | 50.9 | 45.3 | 89.0 | 7.9 | 227 | 19.8 |
|   | 10 | 49.8 | 44.9 | 90.2 | | | |
|   | 20 | 48.6 | 44.0 | 90.5 | | | |
| 7 | 1 | 51.5 | 45.0 | 87.3 | 3.8 | 258 | 9.8 |
|   | 10 | 49.7 | 45.0 | 90.6 | | | |
|   | 20 | 48.4 | 44.1 | 91.1 | | | |
| 8 | 2 | 51.6 | 46.6 | 90.3 | 4.5 | 252 | 11.6 |
|   | 10 | 50.2 | 45.6 | 90.9 | | | |
|   | 20 | 48.8 | 44.5 | 91.1 | | | |
| 9 | 1 | 50.9 | 44.2 | 86.8 | 1.5 | 278 | 4.2 |
|   | 10 | 48.4 | 42.9 | 88.7 | | | |
|   | 20 | 41.9 | 37.5 | 89.5 | | | |
| 10 | 1 | 53.7 | 47.0 | 87.5 | 2.9 | 254 | 8.8 |
|   | 10 | 52.0 | 47.3 | 91.0 | | | |
|   | 20 | 50.6 | 46.4 | 91.7 | | | |

*after passage of 20 days from the starting of the reaction

EXAMPLES 11 THROUGH 13

The procedures of Examples 1 through 10 were repeated in the same manner except that the calcination was not carried out. The composition of the respective components, the temperature for the methyl formate-forming reaction and the obtained results are shown in Table 2.

dium phosphate, respectively, were mixed to form a precipitate of cupric phosphate. Sodium chloride was contained in the mother liquor. This slurry containing cupric phosphate and sodium chloride was mixed with the copper oxide/zinc oxide/aluminum oxide mixture, and the resulting mixture was dried at 115° C. and calcined at 600° C. in an air current. Incidentally, before the calcination, the $CuO/ZnO/Al_2O_3/Cu_3(PO_4)_2$/NaCl molar ratio was 10/0.5/1/0.33/2. By using the so-obtained catalyst, the experiment was carried out in the same manner as in Examples 1 through 10. The obtained results are shown in Table 2.

tate was mixed with alumina sol and zirconium carbonate in such amounts that the Cu/Al/Zr atomic ratio was 10/2/1. The resulting paste was stirred and crushed,

TABLE 2

| Example No. | Composition (molar ratio) | | | | | | Reaction Temperature (°C.) |
|---|---|---|---|---|---|---|---|
| | CuO | ZnO | Al₂O₃ | Component (A) | Component (B) | Component (C) | |
| 11 | 10 | 0.1 | 1 | Zn₃(PO₄)₂ 1 | NaCl 0.2 | — | 300 |
| 12 | 10 | 0.5 | 0.1 | AlPO₄ 3 Zn₃(PO₄)₂ 0.66 | NaCl 0.2 | — | 320 |
| 13 | 10 | 0.5 | 0.5 | AlPO₄ 2 | NaCl 0.2 | Mg₃(PO₄)₂ | 240 |
| 14 | 10 | 0.5 | 1 | — | CuCl₂ 1 | Na₃PO₄ 0.66 | 290 |

| Example No. | Numbers of Elasped Days | Conversion (mole %) of Methanol | Yield (mole %) of Methyl Formate | Selectivity (mole %) of Methyl Formate | Before Reduction | | Powdering Ratio (% by weight) after Reaction * |
|---|---|---|---|---|---|---|---|
| | | | | | Powdering Ratio (% by weight) | Crushing Strength (Kg/cm²) | |
| 11 | 1 | 49.9 | 44.6 | 89.4 | 2.2 | 272 | 5.8 |
| | 10 | 48.4 | 44.3 | 91.5 | | | |
| | 20 | 47.3 | 43.6 | 92.2 | | | |
| 12 | 1 | 60.1 | 50.4 | 83.8 | 6.6 | 253 | 10.2 |
| | 10 | 57.7 | 49.7 | 86.1 | | | |
| | 20 | 54.6 | 48.0 | 87.9 | | | |
| 13 | 1 | 48.9 | 42.9 | 87.8 | 4.6 | 245 | 9.6 |
| | 10 | 46.5 | 41.9 | 90.2 | | | |
| | 20 | 44.1 | 40.5 | 91.8 | | | |
| 14 | 2 | 50.4 | 46.0 | 91.2 | 5.7 | 226 | 14.1 |
| | 10 | 47.5 | 43.9 | 92.5 | | | |
| | 20 | 46.7 | 43.3 | 92.8 | | | |

*after passage of 20 days from the starting of the reaction

COMPARATIVE EXAMPLE 1

An aqueous solution of sodium carbonate was added with stirring to a mixed aqueous solution containing copper nitrate, zinc nitrate and aluminum nitrate at a molar ratio of 10/0.5/2 so that the pH value of the liquid mixture was 9, whereby a precipitate was formed. The precipitate was recovered by filtration and washed, and the washed precipitate was dried at 115° C. for 20 hours and calcined at 700° C. for 3 hours in an air current. Then, about 3% by weight of graphite was added to the calcination product and the mixture was granulated according to the tableting method.

The activity and strength were determined according to the same procedures as in Examples 1 through 10. The obtained results are shown in Table 3.

COMPARATIVE EXAMPLE 2

An aqueous solution of sodium carbonate was added to a mixed aqueous solution containing copper nitrate and zinc nitrate at a molar ratio of 10:0.5 to obtain a coprecipitate of copper and zinc. The coprecipitate was recovered by filtration and washed, and the coprecipitate was mixed with alumina sol and zirconium carbonate in such amounts that the Cu/Al/Zr atomic ratio was 10/2/1. The resulting paste was stirred and crushed, and it was then dried at 115° C. and calcined at 650° C. in an air current. Then, 3% by weight of graphite was added to the calcination product, and the mixture was granulated according to the tableting method.

The activity and strength were determined in the same manner as in Examples 1 through 10. The obtained results are shown in Table 3.

TABLE 3

| Comparative Example No. | Composition (atomic ratio) | | | | Reaction Temperature (°C.) | Number of Elapsed Days | Conversion (mole %) of Methanol | Yield (mole %) of Methyl Formate | Selectivity (mole %) of Methyl Formate | Before Reduction | | Powdering Ratio (% by weight) after Reaction * |
|---|---|---|---|---|---|---|---|---|---|---|---|---|
| | Cu | Zn | Al | Zr | | | | | | Powdering Ratio (% by weight) | Crushing Strength (Kg/cm²) | |
| 1 | 10 | 0.5 | 2 | — | 250 | 1 | 37.3 | 29.6 | 79.4 | 33.3 | 200 | powdered* |
| | | | | | | 10 | 33.6 | 29.2 | 86.9 | | | |
| 2 | 10 | 0.5 | 2 | 1 | 290 | 1 | 48.3 | 42.0 | 87.0 | 9.0 | 186 | 67.2** |
| | | | | | | 10 | 49.4 | 44.0 | 89.0 | | | |
| | | | | | | 20 | 48.6 | 43.7 | 90.0 | | | |

Note
*after passage of 10 days, the catalyst could not be used because of extreme powdering
**after passage of 20 days from the starting of the reaction

What is claimed is:

1. A process for the preparation of a catalyst for the synthesis of methyl formate by dehydrogenating methanol in the gaseous phase, said process being characterized in that (A) at least one phosphate selected from the group consisting of copper phosphates, zinc phosphates and aluminum phosphates, and (B) at least one chloride selected from the group consisting of copper chlorides, zinc chloride, aluminum chloride, alkali metal chlorides and alkaline earth metal chlorides and/or (C) at least one compound selected from the group consisting of alkali metal compounds (exclusive of halides) and alkaline earth metal compounds (exclusive of halides) are added to copper oxide, zinc oxide and aluminum oxide.

2. A process for the preparation of a catalyst according to claim 1, wherein the component (A) is at least one member selected from the group consisting of cupric phosphate, zinc phosphate, aluminum phosphate, aluminum monohydrogenphosphate and aluminum dihydrogen phosphate.

3. A process for the preparation of a catalyst according to claim 1, wherein the component (B) is at least one member selected from the group consisting of cuprous chloride, cupric chloride, zinc chloride, aluminum chloride, sodium chloride, lithium chloride, cesium chloride, potassium chloride, calcium chloride, strontium chloride and barium chloride.

4. A process for the preparation of a catalyst according to claim 1, wherein the component (C) is at least one member selected from the group consisting of alkali metal oxides, alkaline earth metal oxides, alkali metal hydroxides, alkaline earth metal hydroxides, inorganic acid salts of alkali metals, inorganic acid salts of alkaline earth metals, organic acid salts of alkali metal and organic acid salts of alkaline earth metals.

5. A process for the preparation of a catalyst according to any of claims 1 through 4, wherein the component (C) is at least one inorganic acid salt selected from the group consisting of carbonates, phosphates, nitrates and sulfates of alkali metals and alkaline earth metals.

6. A process for the preparation of a catalyst according to any of claims 1 through 4, wherein the component (C) is at least one organic acid salt selected from the group consisting of formates, acetates and oxalates of alkali metals and alkaline earth metals.

7. A process for the preparation of a catalyst according to claim 1, wherein copper oxide, zinc oxide, aluminum oxide, the component (A), the component (B) and the component (C) are used in such amounts that the copper oxide/zinc oxide/aluminum oxide/component (A)/component (B)/component (C) molar ratio is in the range of 10/(0.01 to 10)/(0.01 to 10)/(0.01 to 10)/(0.01 to 10)/(0.01 to 10).

* * * * *